United States Patent
Krauter et al.

(10) Patent No.: US 6,818,720 B2
(45) Date of Patent: Nov. 16, 2004

(54) SUPPORTED HYDROGENATING CATALYST IN POWDER FORM

(75) Inventors: Jürgen Krauter, Dreieich (DE); Michael Gross, Frankfurt am Main (DE); Uwe Packruhn, Frankfurt am Main (DE); Markus Göttlinger, Rodenbach (DE)

(73) Assignee: Degussa AG, Dusseldorf (DE)

( * ) Notice: Subject to any disclaimer, the term of this patent is extended or adjusted under 35 U.S.C. 154(b) by 0 days.

(21) Appl. No.: 10/288,289

(22) Filed: Nov. 6, 2002

(65) Prior Publication Data

US 2003/0100797 A1 May 29, 2003

Related U.S. Application Data

(60) Provisional application No. 60/333,153, filed on Nov. 27, 2001.

(30) Foreign Application Priority Data

Nov. 8, 2001 (DE) .......................... 101 54 811
Apr. 12, 2002 (DE) .......................... 102 16 108

(51) Int. Cl.$^7$ .................. C01G 55/00; C07C 209/36
(52) U.S. Cl. .................. 526/915; 564/421; 564/422; 564/423
(58) Field of Search .................. 526/915; 564/421–423

(56) References Cited

U.S. PATENT DOCUMENTS

| | | |
|---|---|---|
| 2,823,235 A | 2/1958 | Penrose et al. |
| 3,127,356 A | 3/1964 | Hamilton, Jr. |
| 4,212,824 A | 7/1980 | Seagraves et al. |
| 4,426,319 A | 1/1984 | Blanchard et al. |
| 4,719,197 A | 1/1988 | Vogt et al. |
| 5,395,965 A | 3/1995 | Burmeister et al. |
| 5,616,806 A | 4/1997 | Nagata et al. |
| 5,993,762 A | 11/1999 | Rajaram et al. |
| 6,111,140 A | 8/2000 | Buysch et al. |
| 6,140,539 A | 10/2000 | Sander et al. |
| 6,165,635 A | 12/2000 | Auer et al. |

FOREIGN PATENT DOCUMENTS

| | | |
|---|---|---|
| GB | 2112414 A | 7/1983 |
| WO | WO 96/36597 | 11/1996 |

OTHER PUBLICATIONS

Database CAPLUS on STN, Acc. No. 1992:41066, Nagata et al., EP 458006, Nov. 27, 1991, (abstract).*

Yang et al., "Synergic Effect Of Polymer Supported Pd–Pt Bimetallic Catalysts On The Hydrogenation Of Nitroaromatics", Chinese Chemical Letters, vol. 7(7):663–664, (1996).

* cited by examiner

Primary Examiner—Brian Davis
(74) Attorney, Agent, or Firm—Venable LLP; Thomas G. Wiseman

(57) ABSTRACT

Supported, hydrogenating catalyst in powder form containing, as a catalytically active component, a primary precious metal component, a secondary precious metal component and one or more non-precious metal components. It is used for the hydrogenation of nitroaromatics, in particular nitrobenzene and DNT.

7 Claims, No Drawings

SUPPORTED HYDROGENATING CATALYST IN POWDER FORM

This application claims the benefit of U.S. provisional application No. 60/333,153 dated Nov. 27, 2001.

The invention relates to a supported hydrogenating catalyst in powder form, a process for its production and its use in the catalytic hydrogenation of nitroaromatics.

The hydrogenation of aromatic nitro-compounds to amines is one of the major ways of producing amines in industrial chemistry. Today, aromatic amines are central components in the prodution of fine, speciality and even bulk chemicals. Examples in the field of bulk chemicals, in particular, are aniline and toluenediamines (TDA). The catalytic hydrogenation of nitrobenzene to aniline replaced the old Bechamps reduction method, making an important contribution to sustained development. TDA can be regarded as an intermediate for the production of polyurethane foams, being converted in a phosgenation reaction to toluene diisocyanate (TDI), which is processed together with polyalcohols to produce polyurethane foams.

Various processes and catalysts are known for the production of aromatic amines by hydrogenation of the corresponding aromatic nitro-compounds. In addition to the hydrogenation of nitrobenzene to aniline in the gas phase, there are a number of other processes, all of which work in the liquid phase. In addition to supported non-precious metal catalysts and Raney-type catalysts, supported catalysts containing precious metals are also used.

A number of catalysts are known for the catalytic hydrogenation of nitroaromatics, in particular of dinitrotoluene, in the suspension phase.

U.S. Pat. No. 2,823,235 discloses palladium, platinum and palladium-platinum catalysts on black, which are doped with iron.

Very similar catalysts, which contain blacks as supports, are disclosed in U.S. Pat. No. 3,127,356.

U.S. Pat. No. 4,256,671 discloses, in addition to Pd and Pt, also Ni, Ru and Rh as a precious metal component for catalysts used in the catalytic hydrogenation of dinitrotoluenes to toluenediamines.

U.S. Pat. No. 6,096,924 discloses, as a catalytically active component, Rh, Ru, Ir, Pt, Pd, Ni and Co. These metals are applied to powder-form supports. V is used as a doping metal.

DE 199 11 865 A1 discloses a similar system with Ir as the precious metal and V as the doping metal.

Whilst the stated printed publications disclose Pd-, Ir- or Pd—Pt-catalysts, U.S. Pat. No. 4,212,824 discloses a Pt-catalyst on black, which is doped with Fe. Fe and V are the non-precious metals used by far the most frequently for doping.

It is also known that the addition of a few mol-percent of platinum (for example 15 mol %) to supported palladium catalysts produces a positive synergetic effect on activity. This is disclosed in *Pol. Chem. Stosow*. 1981, 25(1), 53–68 or in *Chin. Chem. Lett*. 1996, 7(7), 663–664.

The former printed publication shows that platinum may be present only in a smaller molar quantity than palladium. The optimum is ca. 20 mol % Pt in relation to Pd. If a larger quantity of Pt is used, lower activity is determined.

The object of the present invention is to improve the selectivity and activity of the catalytic hydrogenation of nitroaromatics to aminoaromatics, i.e. to reduce the formation of by-products and to increase the yield of the desired product, through the selection and production of a hydrogenating catalyst.

The invention provides a supported hydrogenating catalyst in powder form, which contains, as catalytically active components, a mixture of a primary precious metal component, a secondary precious metal component and one or more non-precious metal components, wherein either Pt is used as the primary precious metal component with Pd, Ru, Rh as the secondary precious metal component and V, Fe, Mn, Ce and/or Cr as the non-precious metal component, or Pd is used as the primary precious metal component with Ru, Rh as the secondary precious metal component and V, Fe, Mn, Ce and/or Cr as the non-precious metal component or Pd is used as the primary precious metal component with Pt as the secondary precious metal component and Ce and/or Cr as the non-precious metal component.

The hydrogenating catalyst according to the invention can contain, per 100 g dry hydrogenating catalyst, 10 to 50 mmol of the primary precious metal component. The proportion of the secondary precious metal component can be 1 to 60 mol % in relation to the primary precious metal component, preferably 8 to 12 mol % in relation to the primary precious metal component and that of the non-precious metal component 1–700 mol %, preferably 100–600 mol % in relation to the primary precious metal component.

The formation of by-products is influenced only slightly by the ratio of primary to secondary precious metal components which, however has a strong influence on the activity of the catalyst.

As doping metals for the combination Pt as primary precious metal component and Pd, Ru, Rh as secondary precious metal component, V, Fe, Mn, Ce and/or Cr are particularly suitable as the non-precious metal component.

As doping metals for the combination Pd as primary precious metal component and Ru, Rh as secondary precious metal component, V, Fe, Mn, Ce and/or Cr are particularly suitable as the non-precious metal component.

As a doping metal for the combination Pd as primary precious metal component and Pt as secondary precious metal component, Ce and/or Cr are particularly suitable as the non-precious metal component.

Whilst the secondary precious metal component is responsible for the high activity of the catalyst, the non-precious metal component is decisive for selectivity.

The hydrogenating catalyst according to the invention can contain, per 100 g dry hydrogenating catalyst, 15 to 20 mmol of the primary precious metal component, 8 to 12 mol %, in relation to the primary precious metal component, of the secondary precious metal component, and 1 to 600 mol %, in relation to the primary precious metal component, of cerium.

Supports in powder form are used as supports, and these powder supports may be physically activated carbons, chemically activated carbons, blacks, aluminium oxides or silicon oxides, preferably physically activated carbons, chemically activated carbons or blacks.

The invention further provides a process for the production of the hydrogenating catalyst according to the invention, which is characterised in that an aqueous solution containing the primary and secondary precious metal components and the non-precious metal component in dissolved form is added to a suspension of a powder-form support material in water, the primary and secondary precious metal components and the non-precious metal component are deposited on the powder-form support using a base and reduction is optionally carried out using a reducing agent such as for example formaldehyde, hydrazine, hydrogen, sodium tetrahydroborate, formic acid or sodium formate.

Reduction can be carried out at a temperature of 0 to 100° C.

The order in which the support material, water, metal salt solutions and reducing agents are added can also be varied. Optionally, reduction can take place with hydrogen on the dried catalyst. The use of a reducing agent is optional, i.e. the catalyst according to the invention can be separated out from the reaction mixture by filtration, without the addition of a reducing agent, after the primary and secondary precious metal and non-precious metal components have been deposited on the support.

The catalyst according to the invention can be used for the hydrogenation of nitroaromatics. The catalyst according to the invention can be used in particular for the hydrogenation of nitrobenzene to aniline and for the hydrogenation of dinitrotoluenes to toluenediamines.

The catalytic hydrogenation of the nitro-compound can be carried out in the liquid phase as a continuously or discontinuously operated process at pressures of 1 to 100 bar and temperatures of 0 to 250° C. in the presence of the catalyst according to the invention.

The catalytic hydrogenation of the nitro-compound in the liquid phase can be carried out as a continuously or discontinuously operated process at pressures of 1 to 100 bar and temperatures of 0° C. to 200° C. in the presence of the catalyst according to the invention.

The catalytic hydrogenation of nitrobenzene or dinitrotoluenes in the presence of the catalyst according to the invention can be carried out in a continuously or discontinuously operated agitated reactor or in a continuously operated circulating reactor in the presence of a solvent, such as for example methanol or toluene. The solvent can also be a mixture of aniline and water, for the hydrogenation of nitrobenzene, or a mixture of dinitrotoluenes in water, for the hydrogenation of dinitrotoluenes.

The hydrogenation of dinitrotoluenes to toluenediamines can be carried out at temperatures of 70 to 200° C., preferably 90 to 150° C., and pressures of 1 to 100 bar, preferably 10 to 40 bar. If hydrogenation is carried out continuously, the quantity of converted dinitrotoluenes must be replaced by topping up and the product-water mixture must be removed from the reactor.

When using the catalyst according to the invention, a synergetic effect is observed i.e. the addition of the secondary precious metal component increases the activity of the catalyst significantly in comparison with the corresponding catalyst containing no second precious metal.

This could not be expected from the prior art according to the printed publications *Pol. Chem. Stosow.* 1981, 25(1), 53–68 or *Chin. Chem. Lett.* 1996, 7(7), 663–664, as they disclose that the activity of the Pd falls if the proportion of Pt is increased.

Consequently, it is surprising that Pd as a secondary precious metal component has a similar synergetic effect when Pt is used as the primary precious metal component.

There is no reference at all in the literature to particularly high activity of the other metal combinations in the hydrogenation of nitro groups. On the contrary, the use of Rh or Ru as a secondary precious metal component would have been expected to have a negative effect as it is known (see for example P. N. Rylander, Catalytic Hydrogenation in Organic Syntheses, Academic Press, 1979, New York, page 175 ff), that Rh and Ru are highly suitable for hydrogenating aromatic rings and would thus be likely to have poor selectivity (i.e. undesirable secondary reactions). Surprisingly, this is not observed.

EXAMPLES

Catalysts according to the invention and reference catalysts are produced and their catalytic properties in the hydrogenation of nitroaromatics are compared.

Reference Example 1
Pd-containing Trimetallic Catalyst on Black

Production of a Pd—Pt—Fe/SB trimetallic catalyst (1.6% Pd+0.2% Pt+4.0% Fe) with Pd as the primary precious metal component, Pt as the secondary precious metal component and a non-precious metal component according to the prior art. The product Shawinigan Black from Chevron (abbreviated in the catalyst to SB=Shawinigan Black) is used as the black support. The Pd—Pt—Fe/SB (1.6% Pd, 0.2% Pt, 4.0% Fe) catalyst is produced as disclosed in U.S. Pat. No. 3,127,356, Example VII.

Example 1
Trimetallic Catalyst on Black 22.06 g Shawinigan Black (commercial product of Chevron, abbreviated in the catalyst to SB=Shawinigan Black) are suspended in 2000 ml de-ionised water and the suspension is set at a pH of 10 using sodium carbonate solution. A solution of 2 g tetrachloropalladic(II)acid (20%), 0.2 g hexachloroplatinic(IV)acid (25%) und 6.98 g cerium (III)chloride heptahydrate in 200 ml deionised water is added to this suspension. After heating to 80° C. the pH is set at 6.4 using sodium carbonate solution, and the suspension is stirred and filtered. 100 g dry catalyst contains 1.6% Pd, 0.2% Pt and 10.5% Ce. The catalyst is abbreviated to Pd—Pt—Ce/SB (1.6, 0.2, 10.5).

Reference Example 2
Bimetallic Catalyst on Black

The catalyst Pd—Pt/SB (1.6% Pd, 0.2% Pt) is produced as described in example 1, but instead of the quantities given there, 24.69 g Shawinigan Black is used and no cerium salt. 100 g dry catalyst contains 1.6% Pd and 0.2% Pt.

Reference Example 3
Pd-containing Trimetallic Catalyst on Activated Carbon 98.21 g activated carbon are suspended in 500 ml de-ionised water and the suspension is set at a pH of 10 using sodium carbonate solution. 8 g tetrachloropalladic(II) acid (20%), 0.8 g hexachloroplatinic(IV) acid (25%) and 30.39 g iron(III)nitrate-nonahydrate, dissolved in 200 ml de-ionised water are added to this suspension. After heating to 80° C., the pH is set at 6.4 using sodium carbonate solution and the suspension is stirred, reduced with formaldehyde and filtered. 100 g dry catalyst contains 1.6% Pd, 0.2% Pt and 4.2% Fe. The catalyst is abbreviated to Pd—Pt—Fe/AC (1.6, 0.2, 4.2).

Example 2
Pd-containing Trimetallic Catalysts on Activated Carbon

Activated carbon is suspended in 500 ml de-ionised water and the suspension is set at a pH of 10 using sodium carbonate solution. 8 g tetrachloropalladic(II) acid (20%), a solution of the secondary precious metal component and a salt of the non-precious metal component, dissolved in 200 ml de-ionised water are added to this suspension. After heating to 80° C. the pH is set at 6.4 using sodium carbonate solution and the suspension is stirred, reduced with formaldehyde and filtered. The quantities are given in Table 1.

Example 3
Pt-containing Trimetallic Catalysts on Activated Carbon

Activated carbon is suspended in 500 ml de-ionised water and the suspension is set at a pH of 10 using sodium carbonate solution. 11.6 g hexachloroplatinic(IV) acid (25%), a solution of the secondary precious metal component and a salt of the non-precious metal component, each dissolved in 200 ml de-ionised water, are added to this suspension. After heating to 80° C., the pH is set at 6.4 with sodium carbonate solution, and the suspension is stirred, reduced with formaldehyde and filtered. The quantities are given in Table 2.

TABLE 1

Data for Example 2.

| Catalyst | Composition | Quantity of activated carbon | Solution of secondary precious metal component | Salt of non-precious metal component |
|---|---|---|---|---|
| Pd-Ru-Fe/AC | 1.6, 0.1, 4.2 | 98.31 g | $RuCl_3$ (20%) 0.49 g | $Fe(NO_3)_3(H_2O)_9$ 30.39 g |
| Pd-Rh-Fe/AC | 1.6, 0.1, 4.2 | 98.31 g | $RhCl_3$ (20%) 0.5 g | $Fe(NO_3)_3(H_2O)_9$ 30.39 g |
| Pd-Pt-Ce/AC | 1.6, 0.2, 10.5 | 91.63 g | $H_2PtCl_6$ (25%) 0.8 g | $CeCl_3(H_2O)_7$ 27.93 9 |
| Pd-Ru-Ce/AC | 1.6, 0.1, 10.5 | 91.98 g | $RuCl_3$ (20%) 0.49 g | $CeCl_3(H_2O)_7$ 27.93 g |
| Pd-Rh-Ce/AC | 1.6, 0.1, 10.5 | 91.98 g | $RhCl_3$ (20%) 0.5 g | $CeCl_3(H_2O)_7$ 27.93 g |

TABLE 2

Data for Example 3.

| Catalyst | Composition | Quantity of activated carbon | Solution of secondary precious metal component | Salt of non-precious metal component |
|---|---|---|---|---|
| Pt-Ru-Fe/AC | 2.9, 0.1, 4.2 | 96.95 g | $RuCl_3$ (20%) 0.49 g | $Fe(NO_3)_3(H_2O)_9$ 30.39 g |
| Pt-Rh-Fe/AC | 2.9, 0.1, 4.2 | 96.95 g | $RhCl_3$ (20%) 0.5 g | $Fe(NO_3)_3(H_2O)_9$ 30.39 g |
| Pt-Pd-Fe/AC | 2.9, 0.1, 4.2 | 96.95 g | $H_2PdCl_4$ (20%) 0.5 g | $Fe(NO_3)_3(H_2O)_9$ 30.39 g |
| Pt-Ru-Ce/AC | 2.9, 0.1, 10.5 | 90.62 g | $RuCl_3$ (20%) 0.49 g | $CeCl_3(H_2O)_7$ 27.93 g |
| Pt-Rh-Ce/AC | 2.9, 0.1, 10.5 | 90.62 g | $RhCl_3$ (20%) 0.5 g | $CeCl_3(H_2O)_7$ 27.93 g |
| Pt-Pd-Ce/AC | 2.9, 0.2, 10.5 | 90.62 g | $H_2PdCl_4$ (20%) 0.5 g | $CeCl_3(H_2O)_7$ 27.93 g |

The catalysts according to the examples are used in the discontinuous hydrogenation of dinitrotoluene to toluenediamine and the activity and selectivity of the catalysts are determined.

The reaction is carried out in a 0.5 l Hastelloy autoclave. First, 40 g 2,4-Dinitrotoluene, 101 g 2,4-toluenediamine, 59 g water und 1.2 g catalyst (in relation to the solids) are fed into the autoclave. Then, after locking the autoclave, the gas space is flushed first with nitrogen and then with hydrogen and finally a hydrogen pressure of 10 bar is established.

After heating to 120° C., the reaction is started by switching on the stirring mechanism. The end point of the reaction can be determined precisely by the rapid reduction in hydrogen absorption.

Hydrogen absorption is recorded during the reaction. Once the reaction has ended and the reaction mixture has cooled, it is taken up in methanol, filtered and analysed by gas chromatography. This allows the yield of TDA, the conversion of DNT and the quantity of by-products to be determined.

The following can be obtained as by-products: toluidines, diaminobenzenes (called low-boilers) and tars. The term tars describes all compounds which have a longer retention time than the primary product TDA.

Activity is calculated from the absorption of hydrogen during the reaction time in relation to the catalyst mass and is given as ml $H_2$/(min g catalyst). The results are summarised in Table 3, Table 4 and Table 5.

TABLE 3

Pd-containing catalysts on black

| | Catalyst | Charge | Activity [ml $H_2$/min g] | Low boilers [%] | TDA yield [%] | Tars [%] |
|---|---|---|---|---|---|---|
| Reference example 1 | Pd-Pt-Fe/SB | 1.6, 0.2, 4.2 | 1000 | 0.01 | 97.92 | 2.07 |
| Reference example 2 | Pd-Pt/SB | 1.6, 0.2 | 1050 | 0.28 | 98.85 | 0.87 |
| Example 1 | Pd-Pt-Ce/SB | 1.6, 0.2, 10.5 | 1200 | 0.0 | 99.47 | 0.53 |

TABLE 4

Pd-containing trimetallic catalysts on activated carbon

| | Catalyst | Charge | Activity [ml H$_2$/min g] | Low-boilers [%] | TDA yield [%] | Tars [%] |
|---|---|---|---|---|---|---|
| Reference example 3 | Pd-Pt-Fe/AC | 1.6, 0.2, 4.2 | 917 | 0.01 | 97.98 | 2.01 |
| Example 2 | Pd-Ru-Fe/AC | 1.6, 0.1, 4.2 | 913 | 0.01 | 97.8 | 2.19 |
| Example 2 | Pd-Rh-Fe/AC | 1.6, 0.1, 4.2 | 901 | 0.01 | 98.28 | 1.71 |
| Example 2 | Pd-Pt-Ce/AC | 1.6, 0.2, 10.5 | 866 | 0.01 | 99.58 | 0.41 |
| Example 2 | Pd-Ru-Ce/AC | 1.6, 0.1, 10.5 | 777 | 0.01 | 99.64 | 0.35 |
| Example 2 | Pd-Rh-Ce/AC | 1.6, 0.1, 10.5 | 800 | 0.02 | 99.64 | 0.34 |

TABLE 5

Pt-containing trimetallic catalysts on activated carbon

| | Catalyst | Charge | Activity [ml H$_2$/min g] | Low-boilers [%] | TDA yield [%] | Tars [%] |
|---|---|---|---|---|---|---|
| Reference example 3 | Pd-Pt-Fe/AC | 1.6, 0.2, 4.2 | 917 | 0.01 | 97.98 | 2.01 |
| Example 3 | Pt-Ru-Fe/AC | 2.9, 0.1, 4.2 | 923 | 0.01 | 99.38 | 0.61 |
| Example 3 | Pt-Rh-Fe/AC | 2.9, 0.1, 4.2 | 920 | 0.00 | 99.13 | 0.87 |
| Example 3 | Pt-Pd-Fe/AC | 2.9, 0.1, 4.2 | 950 | 0.01 | 99.2 | 0.79 |
| Example 3 | Pt-Ru-Ce/AC | 2.9, 0.1, 10.5 | 895 | 0.05 | 99.61 | 0.39 |
| Example 3 | Pt-Rh-Ce/AC | 2.9, 0.1, 10.5 | | | | |
| Example 3 | Pt-Pd-Ce/AC | 2.9, 0.2, 10.5 | 892 | 0.08 | 99.35 | 0.57 |

What is claimed is:

1. A supported hydrogenating catalyst in powder form comprising a powder form support and as catalytically active components, a mixture of a primary precious metal component, a secondary precious metal component and one or more non-precious metal components, wherein when Pt is the primary precious metal component, Pd, or Ru is the secondary precious metal component and one or more of V, Fe, Mn, Ce and Cr the non-precious metal component, or when Pd is the primary precious metal component, either Ru, or Rh as the secondary precious metal component and one or more of V, Fe, Mn, Ce and Cr is the non-precious metal component or when Pd is the primary precious metal component, Pt is the secondary precious metal component and Ce or Cr or both Ce and Cr are the non-precious metal component.

2. The supported hydrogenating catalyst according to claim 1, wherein the powder form support is selected from physically activated carbons, chemically activated carbons, blacks, aluminium oxides or silicon oxides.

3. The supported hydrogenating catalyst according to claim 1, wherein 100 g dry hydrogenation catalyst contains 10–50 mmol of the primary precious metal component, 1–60 mol %, in relation to the primary precious metal component, of the secondary precious metal component, and 1–700 mol %, in relation to the primary precious metal component, of the non-precious metal component.

4. The supported hydrogenting catalyst according to claim 1, wherein 100 g dry hydrogenating catalyst contains 15–20 mmol of the primary precious metal component, 8–12 mol %, in relation to the primary precious metal component, of the secondary precious metal component and 1–600 mol %, in relation to the primary precious metal component, of cerium.

5. A process for the production of a hydrogenating catalyst according to claim 1, comprising adding an aqueous solution containing the primary precious metal component, the secondary precious metal component and the non-precious metal component to a suspension of a powder-form support in water, depositing the primary and secondary precious metal components and the non-precious metal component on the powder-form support material in the presence of a base and optionally reducing the deposited metal components with a reducing agent.

6. A process for the production of aniline, comprising hygrogenating a nitro-compound precursor in the liquid phase at pressures of 1 to 100 bar and temperatures of 0° C. to 200° C. in the presence of a supported catalyst in powder form comprising a powder form support and as catalytically active components, a mixture of a primary precious metal component, a secondary precious metal component and one or more non-precious metal components, wherein when Pt is the primary precious metal component, Pd, Ru, or Rh is the secondary precious metal component and one or more of V, Fe, Mn, Ce and Cr the non-precious metal component, or when Pd is the primary precious metal component, either Ru, or Rh as the secondary precious metal component and one or more of V, Fe, Mn, Ce and Cr is the non-precious metal component or when Pd is the primary precious metal component, Pt is the secondary precious metal component and Ce or Cr or both Ce and Cr are the non-precious metal component.

7. A process for the production of toluenediamines, comprising hygrogenating a nitro-compound precursor in the liquid phase at pressures of 1 to 100 bar and temperatures of 0° C. to 200° C. in the presence of a supported catalyst in powder form comprising a powder form support and as catalytically active components, a mixture of a primary precious metal component, a secondary precious metal component and one or more non-precious metal components, wherein when Pt is the primary precious metal component, Pd, Ru, or Rh is the secondary precious metal component and one or more of V, Fe, Mn, Ce and Cr the non-precious metal component, or when Pd is the primary precious metal component, either Ru, or Rh as the secondary precious metal component and one or more of V, Fe, Mn, Ce and Cr is the non-precious metal component or when Pd is the primary precious metal component, Pt is the secondary precious metal component and Ce or Cr or both Ce and Cr are the non-precious metal component.

* * * * *